(12) United States Patent
Sakuragi

(10) Patent No.: US 8,422,752 B2
(45) Date of Patent: Apr. 16, 2013

(54) DIAGNOSIS ASSISTING APPARATUS, DIAGNOSIS ASSISTING METHOD, AND STORAGE MEDIUM IN WHICH A DIAGNOSIS ASSISTING PROGRAM IS RECORDED

(75) Inventor: Futoshi Sakuragi, Minato-ku (JP)

(73) Assignee: FUJIFILM Corporation, Tokyo (JP)

( * ) Notice: Subject to any disclaimer, the term of this patent is extended or adjusted under 35 U.S.C. 154(b) by 537 days.

(21) Appl. No.: 12/828,704

(22) Filed: Jul. 1, 2010

(65) Prior Publication Data

US 2011/0001761 A1    Jan. 6, 2011

(30) Foreign Application Priority Data

Jul. 3, 2009  (JP) .................................. 2009-158434
Mar. 31, 2010  (JP) .................................. 2010-083139

(51) Int. Cl.
*G06K 9/00*       (2006.01)

(52) U.S. Cl.
USPC ....................................................... 382/128

(58) Field of Classification Search .......... 382/128–134; 128/920–925; 356/39–49; 600/407–414, 600/424–426; 345/581–618
See application file for complete search history.

(56) References Cited

U.S. PATENT DOCUMENTS

| | | |
|---|---|---|
| 2005/0008209 A1 | 1/2005 | Matsumoto |
| 2008/0044080 A1 | 2/2008 | Li |
| 2008/0312527 A1 | 12/2008 | Masumoto et al. |

FOREIGN PATENT DOCUMENTS

| | | |
|---|---|---|
| EP | 2 130 490 A1 | 12/2009 |
| JP | 2005-27999 A | 2/2005 |
| JP | 2007-307358 A | 11/2007 |
| JP | 2008-253753 A | 10/2008 |
| JP | 2008-289799 A | 12/2008 |
| JP | 2009-18005 A | 1/2009 |
| JP | 2009-69895 A | 4/2009 |

OTHER PUBLICATIONS

M.A. Termeer, et al., "Patient-Specific Coronary Artery Supply Territory AHA Diagrams", TU Wien, 12th Annual SCMR Scientific Sessions-2009, Jan. 2009, pp. 164-165, http://www.cg.tuwien.ac.at/research/publications/2009/termeer-2009-scmr/.

*Primary Examiner* — Atiba O Fitzpatrick
(74) *Attorney, Agent, or Firm* — Sughrue Mion, PLLC

(57) ABSTRACT

One or more blood vessel regions that represent one or more blood vessels that govern the function of an organ are extracted from a three dimensional anatomical image that represents the three dimensional shape of the organ. Next, blood vessel governed regions, the functions of which are governed by a single blood vessel, are estimated, based on each blood vessel region, while regions other than the blood vessel governed regions are estimated to be non governed regions. Index values to be indices of diagnosis are calculated by analyzing evaluation values that constitute a three dimensional functional image, without using the evaluation values included in the non governed regions. Then, the calculated index values are output to a display screen or the like.

14 Claims, 11 Drawing Sheets

FIG.14
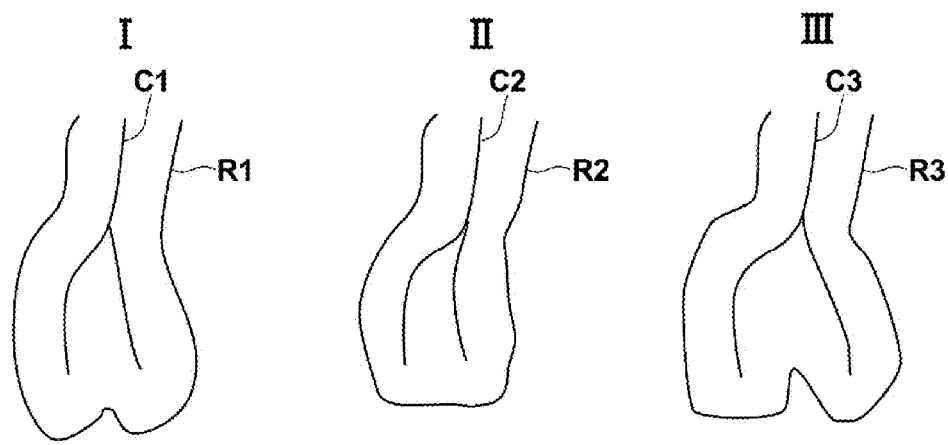
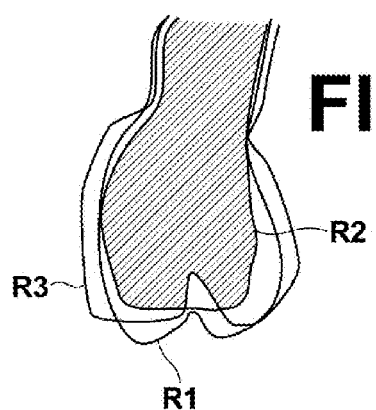
FIG.15A
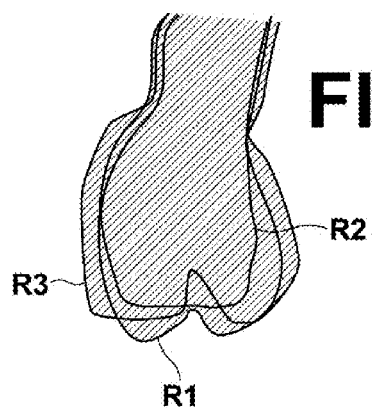
FIG.15B

DIAGNOSIS ASSISTING APPARATUS, DIAGNOSIS ASSISTING METHOD, AND STORAGE MEDIUM IN WHICH A DIAGNOSIS ASSISTING PROGRAM IS RECORDED

BACKGROUND OF THE INVENTION

1. Field of the Invention

The present invention is related to a diagnosis assisting apparatus, a diagnosis assisting method, and a storage medium, in which a diagnosis assisting computer program is recorded, that assist diagnosis by automatically analyzing the functions of organs using three dimensional image data, and by displaying index values which are obtained as a result of the analysis.

2. Description of the Related Art

There are known apparatuses that aid image diagnosis by radiologists, that analyze the states and motions of organs of subjects, based on three dimensional data obtained by imaging the subjects, and display the analysis results in a form suited for diagnosis on screens. A function that calculates evaluation indices of cardiac function (amount of myocardial wall activity, variations in myocardial wall thickness, etc.) based on three dimensional data obtained in temporal sequences is known as an analyzing function of cardiac activity. These evaluation indices are calculated for each of a plurality of cross sections, which are set to be perpendicular to an axis that passes through the base of the heart (the upper portion of the heart where blood vessels are connected) to the apex of the heart (the lower portion of the heart shaped as an apex). The calculated evaluation indices are generally displayed three dimensionally to match the shape of the heart. Meanwhile, bulls eye images, in which the evaluation indices for each cross section are arranged along the circumference of concentric circles having different radii, are known as a method for two dimensionally displaying the analysis results (refer to Japanese Unexamined Patent Publication No. 2009-018005, for example).

In addition, a function of displaying images of coronary arteries overlapped on the bulls eye images has also been proposed (refer to Japanese Unexamined Patent Publication Nos. 2005-027999 (corresponding to U.S. Patent Application Publication No. 20050008209) and 2008-253753 (corresponding to European Patent Publication No. 2130490), for example). Abnormalities in cardiac activity (such as myocardial infarction) are often caused by abnormalities (such as occlusions) of the coronary arteries that supply oxygen and nutrients to the myocardial muscles. Therefore, by observing the shapes of the coronary arteries along with the evaluation values of cardiac functions, judging which coronary artery is the cause of an abnormality in cardiac function can be facilitated.

A method, in which a myocardial region is sectioned into a region close to the right coronary artery (RCA), a region close to the left anterior descending artery (LAD), and a region close to the left circumflex coronary artery (LCX), and cardiac functions are analyzed in units of the sectioned regions, has been proposed. The regions are commonly sectioned by drawing boundary lines having predetermined shapes at predetermined positions. In addition, a method has also been proposed that determines optimal boundaries for each subject, by applying the Voronoi algorithm (M. A. Termeer et al., "Patient-Specific Coronary Artery Supply Territory AHA Diagrams", TU Wien, 12th Annual SCMR Scientific Sessions—2009, pp. 164-165, January 2009; http://www.cg.tuwien.ac.at/research/publications/2009/termeer-2 009-scmr/). According to these methods, coronary arteries which are suspected to have abnormalities can be specified to a degree, based on the analysis results of each of the regions.

In the method that sections the myocardial region and analyzes the sectioned regions, new index values (for example, an average value of evaluation values within the sectioned regions) for evaluating cardiac functions in units of the sectioned regions are derived, and whether each sectioned region is functioning properly is judged based on the index values. However, there are cases that cardiac muscles in the vicinities of the boundaries of the sectioned regions receive oxygen and nutrients from two to three coronary arteries. Therefore, the evaluation values in the vicinities of the boundaries do not necessarily reflect the influence that individual coronary arteries impart on myocardial function. For this reason, it is not preferable to employ all of the evaluation values which are included in the sectioned regions during calculation of the index values, from the viewpoint of accuracy of analysis.

SUMMARY OF THE INVENTION

The present invention has been developed in view of the foregoing circumstances. It is an object of the present invention to perform accurate analysis and to obtain appropriate index values, when analyzing evaluation values that represent the functions of an organ, to derive index values that represent the functions of each region of the organ. Further, it is another object of the present invention to display the obtained index values to physicians, to facilitate specification of a coronary artery which is suspected of being abnormal, to assist diagnosis by the physicians.

A diagnosis assisting apparatus of the present invention is equipped with: an image storage means, a blood vessel region extracting means, a blood vessel governed region estimating means, an index value calculating means, and an output control means. A diagnosis assisting program, which is stored in a computer readable non-transitory storage medium of the present invention, causes at least one computer to execute the processes of each of the aforementioned means. The program is provided to users by being recorded in storage media such as CD-ROM's and DVD's, by being recorded in a non-transitory storage unit attached to a server computer in a downloadable state, or by being recorded in non-transitory network storage in a downloadable state. A diagnosis assisting method of the present invention is a method that assists diagnosis, by causing at least one computer to execute the processes of each of the aforementioned means.

The image storage means stores three dimensional functional images, in which evaluation data for evaluating the functions of organs are arranged three dimensionally along the shapes of the organs, and also stores three dimensional anatomical images that represent the three dimensional structures of the organs. Specifically, an internal memory of a computer that functions as the diagnosis assisting apparatus, a hard disk of the computer, an external storage device which is directly connected to the computer directly or via a network, an external storage device which is directly connected to the computer via a network, etc. function as the image storage means. The three dimensional functional images are represented by volume data, in which voxel data represent evaluation values (such as values that represent the activity and biological reactions of organs), employed to judge whether organs are functioning properly. The three dimensional anatomical images are represented by volume data, in which voxel data represent values that represent the anatomical structures of organs.

The blood vessel region extracting means extracts one or a plurality of blood vessel regions that govern the functions of the organs from within the three dimensional anatomical image. For example, the blood vessel region extracting means extracts blood vessel regions that represent branched blood vessels and are constituted by Nb (Nb is an integer having a value of at least 1) main branched regions from the three dimensional anatomical images. To govern the function of an organ refers to maintaining normal function of the organ, by supplying oxygen and nutrients to the organ. For example, the blood vessel that governs the function of an organ is the coronary artery in the case of the heart, the portal vein in the case of the liver, and the cerebral artery in the case of the brain. Note that in the present specification, comparatively thick blood vessels having individual names are referred to as main branches. For example, the coronary artery is constituted by two main branches, the right coronary artery and the left coronary artery. However, the ranges of blood vessels which are designated as single main branches are arbitrary. For example, in the case of the coronary artery, the left anterior descending artery and the left circumflex coronary artery may be designated as main branches.

The blood vessel governed region estimating means blood estimates vessel governed regions within which organ functions are governed by the blood vessels and estimates regions other than the blood vessel governed regions as non governed regions, based on each of the blood vessel regions. For example, the blood vessel governed region estimating means estimates blood vessel governed regions within which organ functions are governed by Nb main branched regions that constitute a blood vessel region, based on each of the Nb main branched regions, and estimates regions other than the blood vessel governed regions as non governed regions.

The index value calculating means calculates index values to be indices of diagnosis by analyzing the evaluation values that constitute the three dimensional functional image. The index value calculating means calculates the index values without using the evaluation values included in the non governed regions. In other words, the index values are derived only from evaluation values which are included in the blood vessel governed regions. Note that in the present specification, the values of data that constitute the three dimensional functional images and functional bulls eye images are referred to as "evaluation values", and values obtained as a result of analysis administered with respect to the evaluation values are referred to as "index values". Analysis includes all processes that derive index values which are useful for diagnosis from the evaluation values. Examples of such analysis include: a process for calculating mean values (including weighted mean values) of the evaluation values; a process for obtaining the maximum evaluation value; and a process for obtaining the minimum evaluation value.

The output control means controls all output, such as: output to a display device (monitor display); output to a printing apparatus (printout); and output to a data recording device (recording onto media). The output control means controls the output format, the output timing, and the like of the index values calculated by the index value calculating means. Outputting the index values along with images is a preferred output format. Alternatively, only the index values may be output.

In the configuration described above, regions, which are unclear as to what blood vessel governs the functions thereof, are estimated as non governed regions, and the evaluation values included in the non governed regions are not employed to calculate the index values for diagnosis. Accordingly, the index values which are calculated for the blood vessel governed regions are values that accurately reflect the influence imparted onto the regions by each blood vessel. By referring to these index values, accurate judgment regarding whether abnormalities in organ functions are caused by abnormalities in blood vessels is facilitated. In addition, in the case that abnormalities in organ functions are caused by abnormalities in blood vessels, the blood vessel which is the cause of the abnormality can be easily specified.

Note that the image storage means may store Nt (Nt is an integer having a value of at least 2) three dimensional anatomical images, each of which represents the structures of each organ in a different phase. For example, a plurality of three dimensional anatomical images having different phases are generally obtained during examination of the heart, and therefore, a plurality of three dimensional anatomical images are stored for each single examination. In the case that Nt three dimensional anatomical images are stored for a single organ, the aforementioned processes may be administered onto a selected one of the three dimensional anatomical images. However, it is preferable for the blood vessel region extracting means to extract blood vessel regions from each of the Nt three dimensional anatomical images.

In this case, it is preferable for the blood vessel governed region estimating means to estimate the blood vessel governed regions by the following procedures. First, blood vessel governed regions are estimated for each of the Nt extracted blood vessel regions, by executing the aforementioned estimating process. That is, the blood vessel governed region estimating means estimates blood vessel governed regions, within which organ functions are governed by Nb main branched regions that constitute each of the Nt extracted blood vessel regions, based on each of the Nb main branched regions, and obtains one of a product and a sum of the Nt blood vessel governed regions within different phases, which are estimated for each of the Nb main branched regions within the Nt blood vessel regions. Thereafter, the blood vessel governed region estimating means estimates one of the product and the sum to be the blood vessel governed regions governed by blood vessels represented by the main branched regions.

In organs having large amounts of activity, such as the heart, the positions of the blood vessels change according to the movement of the organ, and accompanying the changes in position, the regions which are governed by the blood vessel also change. For this reason, there are cases that the estimation results will vary depending on which phase the selected three dimensional anatomical image is in, in the case that the blood vessel governed regions are estimated employing a single three dimensional anatomical image. In contrast, by designating the sum of the Nt blood vessel governed regions of different phases as the blood vessel governed regions as described above, the index values can be derived with respect to a region which is governed by the main branch in at least one of the phases. Alternatively, by designating the product of the Nt blood vessel governed regions of different phases as the blood vessel governed regions, the index values can be derived regarding the region which is governed by the blood vessels regardless of the phase.

Note that it is preferable for the evaluation values that constitute the three dimensional functional images to be weighted according to the number of overlapping blood vessel governed regions within different phases, in the case that the blood vessel governed regions are sums of the Nt blood vessel governed regions within different phases. By performing the weighting, the evaluation values of regions which are always governed by the main branches regardless of the phase become relatively greater, while the evaluation values of regions which are only governed by the main branches during a portion of phases become relatively smaller. Therefore, the calculated index values become values that more accurately reflect the influence imparted on the functions of the organs by the main branches.

It is preferable for the blood vessel governed region estimating means to estimate each blood vessel governed region such that one blood vessel governed region does not overlap another blood vessel governed region, in the case that the blood vessel regions are constituted by two or more main branched regions. It is possible to analyze the relevance of the blood vessels as a whole and the functions of the organs, even if a plurality of blood vessel governed regions overlap each other. However, in cases that examinations are performed to determine which coronary artery is causing deteriorations in cardiac function and the like, it is necessary to clearly define regions which are governed by each blood vessel, to which influence from other blood vessels is not imparted, in order to analyze the relationship between each blood vessel and the organ function individually.

The width of the blood vessel governed regions may be uniform regardless of the thickness of the blood vessels. However, it is considered that the range that a blood vessel governs is larger for thicker blood vessels. Therefore, the blood vessel governed regions may be set to become wider at locations where the blood vessels are thicker. Here, the width of the region refers to the distance between the boundaries of the blood vessel governed regions and the non governed regions, and the walls of the blood vessels (or the centerlines of the blood vessels).

It is preferable for the index value calculating means to calculate index values for each of two or more blood vessel governed regions, in the case that the blood vessel regions are constituted by two or more main branched regions. Alternatively, only one index value may be derived for a plurality of blood vessel governed regions.

It is preferable for the diagnosis assisting apparatus to be further equipped with: a bulls eye image generating means, for generating bulls eye images with respect to each of the three dimensional functional images and the three dimensional anatomical images. In this case, it is preferable for the output control means to cause a bulls eye image of the three dimensional functional image and the bulls eye image of the three dimensional anatomical image to be displayed overlapped on each other on the screen of a display device, and also to cause the index values calculated by the index value calculating means to be displayed on the screen. Alternatively, the three dimensional functional image and the three dimensional anatomical image may be displayed overlapped on each other instead of the bulls eye images, and the index values may be displayed about the periphery thereof.

It is preferable for the blood vessel governed region estimating means to display the estimated blood vessel governed regions on the screen of a display device, to detect user operations performed with respect to the screen, and to update the blood vessel governed regions based on the detected operations. In addition, it is preferable for the blood vessel region extracting means to display the extracted blood vessel regions on the screen of a display device, to detect user operations performed with respect to the screen, and to correct the extracted blood vessel regions based on the detected operations. It is preferable for the blood vessel governed region estimating means to estimate the blood vessel governed regions and the non governed regions based on corrected blood vessel regions, in the case that correction of the blood vessel regions is performed. This configuration is preferable, because there are cases in which the image quality of the three dimensional anatomical images is poor, and the computer cannot perform accurate extraction or estimation.

The index values regarding the blood vessel governed regions calculated by the diagnosis assisting apparatus, the diagnosis assisting method, and the diagnosis assisting program of the present invention are values that accurately reflect the influence imparted onto the regions by the blood vessels. Thereby, judgments by physicians and radiology technicians regarding whether abnormalities in the functions of organs are caused by abnormalities in blood vessels are facilitated. Further, the blood vessel which is suspected of being abnormal can be easily specified.

BRIEF DESCRIPTION OF THE DRAWINGS

FIG. 14 is a diagram that illustrates examples of coronary artery governed regions of different phases.

FIG. 15A is a diagram that illustrates an example of a product of coronary artery governed regions of different phases.

FIG. 15B is a diagram that illustrates an example of a sum of coronary artery governed regions of different phases.

DESCRIPTION OF THE PREFERRED EMBODIMENTS

Hereinafter, embodiments of the present invention will be described in detail with reference to the attached drawings.

In the embodiments to be described below, the diagnosis assisting apparatus is a computer, in which a diagnosis assisting program according to each embodiment is installed. The computer may be a work station or a personal computer which is directly operated by a physician who performs diagnoses. Alternatively, the computer may be a server computer which is connected to such a work station or personal computer via a network. The diagnosis assisting programs are distributed by being recorded in storage media such as CD-ROM's and DVD's, and installed in the computer from the storage media. Alternatively, the diagnosis assisting program is recorded in a storage unit attached to a server computer in a state in which it is accessible from the exterior, or recorded in network storage in a state in which it is accessible from the exterior, and downloaded to and installed in computer utilized by the physician as necessary.

Embodiment 1

Figure 1:
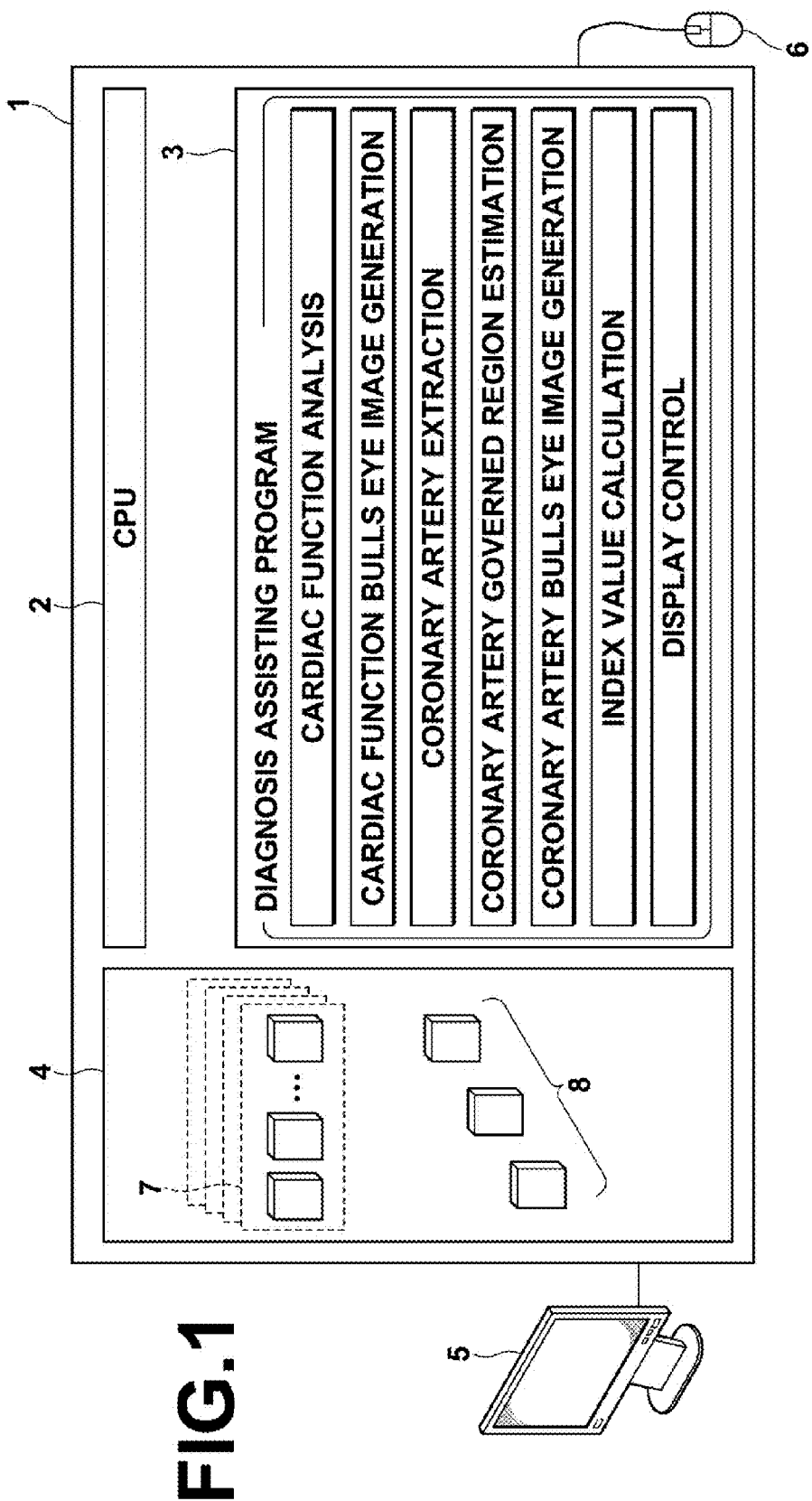
FIG. 1 is a diagram that illustrates the schematic structure of a diagnosis assisting apparatus according to an embodiment of the present invention.

FIG. 1 is a diagram that illustrates the schematic structure of a diagnosis assisting apparatus 1, which is realized by installing a diagnosis assisting program into a work station. As illustrated in FIG. 1, the diagnosis assisting apparatus 1 is equipped with a CPU 2, a memory 3, and a storage 4, as is standard for a work station. In addition, a display 5 and input devices, such as a mouse 6, are connected to the diagnosis assisting apparatus 1.

Volume data, which are constituted by slice data output from CT (Computed Tomography) apparatuses and MRI (Magnetic Resonance Imaging) apparatuses, volume data, which are output from MSCT (Multi Slice Computed Tomography) apparatuses and cone beam CT apparatuses, and the like, are stored in the storage 4 as three dimensional anatomical images 7. The volume data are obtained by imaging a subject a plurality of times with predetermined temporal intervals therebetween. A plurality of sets of volume data regarding a single subject in temporal sequence and for each modality are stored in the storage 4.

SPECT (Single Photon Emission Computed Tomography) images output from SPECT imaging apparatuses, functional images generated by analyzing volume data output from MSCT apparatuses, and the like are also stored in the storage 4 as three dimensional functional images 8. As will be described later, the function of analyzing the volume data (cardiac function analyzing function) is provided as a function of the diagnosis assisting program of the present embodiment.

The diagnosis assisting program and data (processing parameters and the like) which are referred to by the diagnosis assisting program are stored in the memory 3. The diagnosis assisting program defines: a cardiac function analyzing process; a cardiac function bulls eye image generating process; a coronary artery extracting process; a coronary artery governed region estimating process; a coronary artery bulls eye image generating process; a distance calculating process; and a display control process as processes to be executed by the CPU 2. The general purpose work station functions as a cardiac function analyzing means, a cardiac function bulls eye image generating means, a coronary artery extracting means, a coronary artery governed region estimating means, a coronary artery bulls eye image generating means, a distance calculating means, and a display control means, by the CPU 2 executing these processes according to the program.

Figure 2:
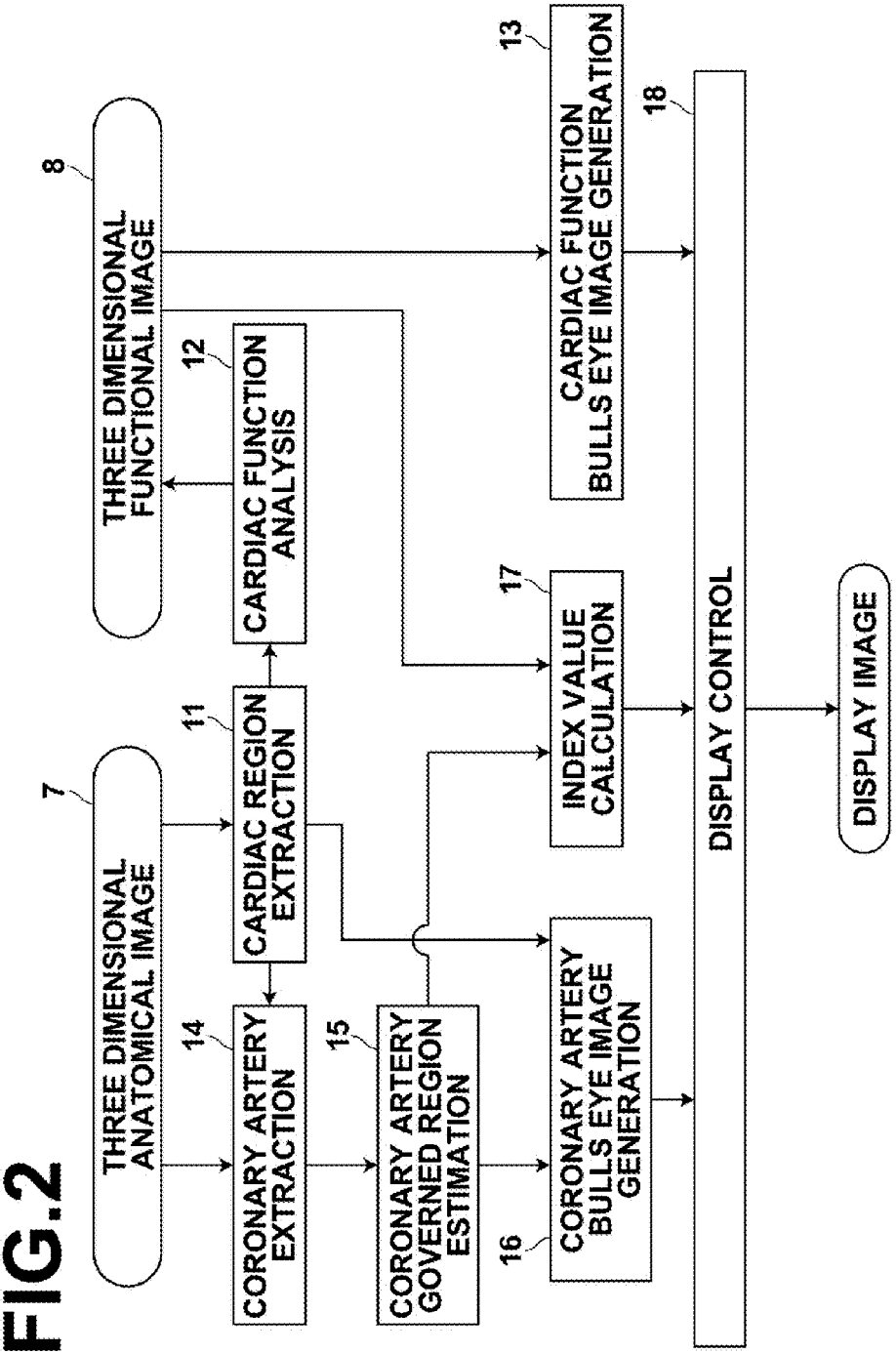
FIG. 2 is a diagram that illustrates the outline of processes, which are performed by the diagnosis assisting apparatus of FIG. 1.

FIG. 2 is a diagram that illustrates the outline of processes, which are executed by the diagnosis assisting program. When it is detected that a cardiac function diagnosis assisting function is selected from a selection menu, the diagnosis assisting apparatus 1 displays a list of subject ID's. When a selection operation by a user is detected, the diagnosis assisting apparatus 1 loads image files related to the selected subject into the memory 3. In the case that a plurality of types of examinations (for example, CT examination and SPECT examination) had been performed on the subject and three dimensional anatomical images 7 and a three dimensional functional image 8 are both stored in the storage 4, the two types of images are loaded into the memory 3. On the other hand, in the case that only three dimensional anatomical images 7 are stored in the storage 4, the three dimensional anatomical images 7 are loaded into the memory 3.

After the three dimensional anatomical images 7 are loaded into the memory 3, the diagnosis assisting apparatus 1 executes a cardiac region extracting process 11 with respect to the three dimensional anatomical image 7. A cardiac region (the entire heart) is extracted, and then a left ventricle region is extracted from the cardiac region in the cardiac region extracting process 11. In the present embodiment, each of the regions is extracted by determining the outlines of each region. Specifically, the diagnosis assisting apparatus 1 calculates features that represent likeliness of being the outline of the heart and features that represent likeliness of being the outline of the left ventricle from the values of voxel data that constitute the three dimensional anatomical image 7. Then, the calculated features are evaluated using evaluations functions which are obtained in advance by machine learning, and judgments are made regarding whether the voxel data represents the outline of the heart, and whether the voxel data represents the outline of the left ventricle (the boundary surface between the left ventricle and myocardial muscle). By repeating these judgments, voxel data that represent the outline of the entire heart and voxel data that represent the outline of the left ventricle are extracted. In the present embodiment, the Adaboost algorithm is employed to obtain the evaluation functions. The details of the outline determination method are disclosed, for example, in Japanese Unexamined Patent Publication No. 2007-307358 (corresponding to U.S. Patent Application Publication No. 20080044080). Note that the extraction of the cardiac region may be performed by other machine learning methods or statistical analysis methods, such as the linear judgment method, neural networks, and support vector machines.

Figure 3:
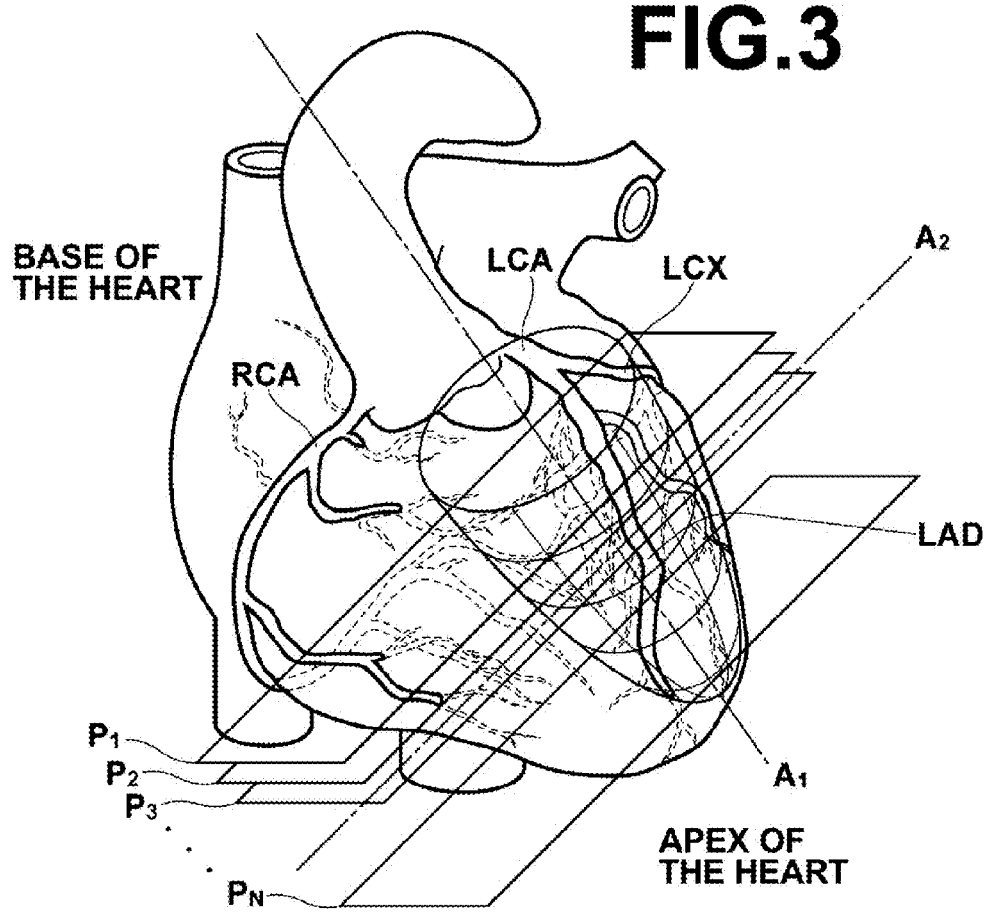
FIG. 3 is a diagram that illustrates a long axis and cross sections, which are set in a cardiac function analyzing process.
Figure 4:
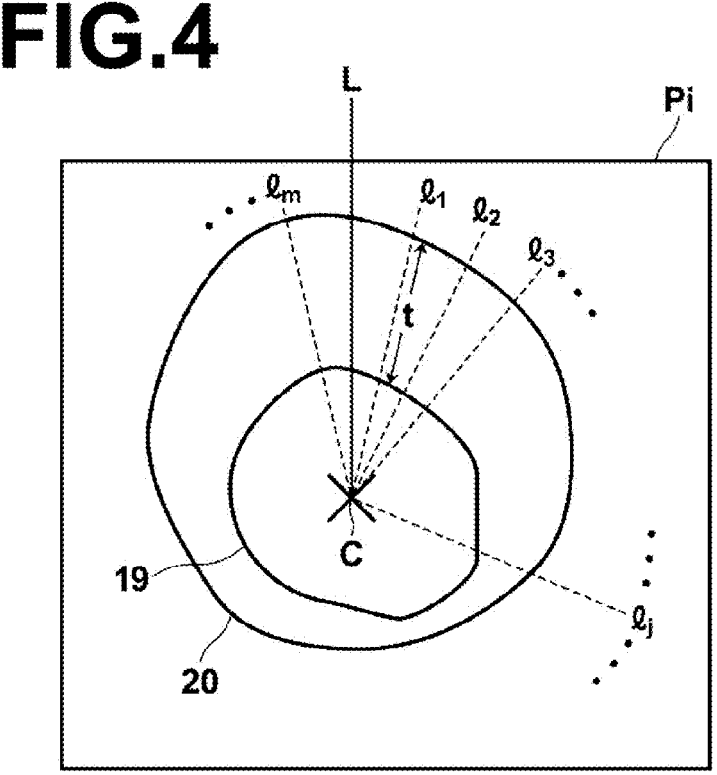
FIG. 4 is a diagram that illustrates an example of evaluation data, which are calculated in the cardiac function analyzing process.

Next, the diagnosis assisting apparatus 1 executes a cardiac function analyzing process 12. However, the cardiac function analyzing process 12 is not executed in the case that a three dimensional functional image 8, such as a SPECT image, is stored in the memory 3. Hereinafter, the cardiac function analyzing process 12 will be described with reference to FIG. 3 and FIG. 4. Note that as illustrated in FIG. 3, the left coronary artery LCA branches into a left anterior descending artery (LAD), which extends downward along the front surface of the heart, and the left circumflex coronary artery LCX, which extends downward along the left side surface of the heart. In contrast, the right coronary artery RCA extends downward along the right side surface of the heart.

As illustrated in FIG. 3, during the cardiac function analyzing process 12, the diagnosis assisting apparatus 1 sets a long axis A1 that connects the base of the heart, the apex of the heart, and the center of the left ventricle, and a short axis A2 that perpendicularly intersects the long axis A1. in the present embodiment, the long axis is set automatically, by calculating the positional coordinates of the apex of the heart and the center of the left ventricle, from the results of the cardiac region extracting process. The short axis A2 is set such that it passes through the center of the left ventricle and is perpendicular to the long axis A1. However, a configuration is adopted such that the position and direction of the automatically set long axis is correctable by user operations. In the present embodiment, the automatically set long axis is displayed along with an image of the cardiac region on a screen.

The position and direction of the long axis is enabled to be changed by click and drag operations, or by rotation operations.

Thereafter, the diagnosis assisting apparatus 1 sets a plurality of cross sections P1 through Pn that perpendicularly intersect the set long axis. Then, the diagnosis assisting apparatus 1 defines a plurality of line segments l1 through lm within each of the cross sections Pi that extend radially from the points at which the long axis A1 and the cross sections Pi intersect. Next, the coordinate values of the boundary 19 between the left ventricle and myocardial muscle along each line segment li and the coordinate values of the outer wall 20 of the myocardial muscle along each line segment li are obtained, and the myocardial wall thickness t along each line segment li is calculated from these coordinate values. This process is repeated with respect to a plurality of three dimensional anatomical images in temporal series, and the differences of the coordinate values among images are obtained. Thereby, a plurality of types of evaluation values, such as the amount of myocardial wall activity, variations in myocardial wall thickness, etc., for evaluating whether cardiac activity is normal, are calculated. A three dimensional functional image 8, in which evaluation values regarding cardiac functions are arranged along the shape of the heart, is generated by this process. The generated three dimensional functional image 8 is stored in the memory 3. Note that the details of a method for generating a three dimensional functional image by analyzing three dimensional anatomical images are disclosed, for example, in Japanese Unexamined Patent Publication No. 2008-289799 (corresponding to U.S. Patent Application Publication No. 20080312527).

Figure 5:
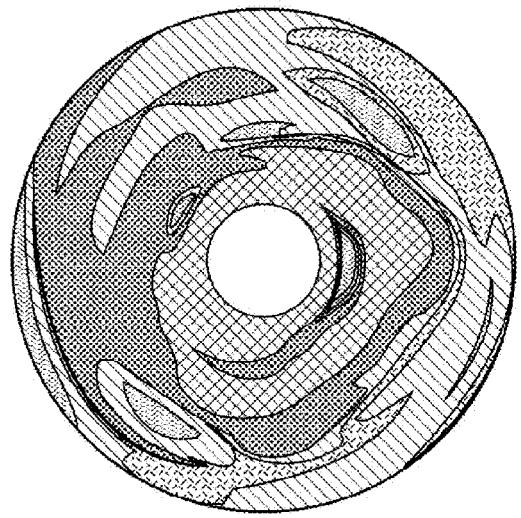
FIG. 5 is a diagram that illustrates an example of a cardiac function bulls eye image.

Next, the diagnosis assisting apparatus 1 executes a cardiac function bulls eye image generating process 13. In the cardiac function bulls eye image generating process 13, the diagnosis assisting apparatus 1 generates a cardiac function bulls eye image, by arranging the evaluation values, which are included in the plurality of cross sections P1 through Pn (in the case that cardiac function analysis was performed, the evaluation values which were calculated at each cross section of the three dimensional anatomical image 7), along the circumferences of concentric circles of which the radius differs for each cross section. In the present embodiment, the apex of the heart is set as the center of the concentric circles, the evaluation value of the cross section Pn, which is closest to the apex of the heart, are arranged along the circumference of a circle having the smallest radius, and the evaluation value of the cross section P1, which is furthest from the apex of the heart, are arranged along the circumference of a circle having the largest radius. FIG. 5 is a diagram that illustrates an example of a cardiac function bulls eye image which is generated by this process.

Note that in the case that the three dimensional functional image 8 is not obtained by the cardiac function analyzing process 12, but is an image, such as a SPECT image which is output from an imaging apparatus that generates functional images, the long axis, the short axis, the cross sections, and the radial line segments are set within the three dimensional functional image 8 in the same manner as that for the three dimensional anatomical images 7, then the aforementioned process is executed, to generate the cardiac function bulls eye image. In this case, it is desirable for positioning to be performed between the coordinates of the three dimensional anatomical images 7 and the three dimensional functional image 8.

The diagnosis assisting apparatus 1 executes a coronary artery extracting process 14 with respect to the cardiac region extracted by the cardiac region extracting process 11 and the vicinity thereof within the three dimensional anatomical image 7. This process may be executed in parallel with the cardiac function analyzing process or the cardiac function bulls eye image generating process.

In the present embodiment, the coronary arteries are extracted by the method disclosed in Japanese Patent Application No. 2009-069895. In this method, first, a rectangular parallelepiped region that includes the cardiac region is set as a search range. Next, linear structures which are included in the search range are searched for based on a predetermined algorithm. Further, points which are estimated to be points along the cores of coronary arteries are detected, based on the linear structures detected by the search. In the following description, the points which are estimated to be points along the cores of coronary arteries will be referred to as candidate points or nodes.

The search for the linear structures is performed by calculating unique values of a 3×3 Hessian matrix for each local region within the search range. In regions that include linear structures, one of the three unique values of the Hessian matrix becomes a value close to zero, while the other two values will be relatively greater values. In addition, the unique vector that corresponds to the unique value close to zero indicates the direction of the main axis of the linear structures. In the coronary artery extracting process 14, this relationship is utilized to judge likelihoods of being linear structures based on the unique values of a Hessian matrix for each local region. In local regions in which linear structures are discriminated, the center points thereof are detected as candidate points.

Next, the candidate points which are detected by the search are linked based on a predetermined algorithm. Thereby, tree structures constituted by the candidate points and blood vessel branches (edges) that connect the candidate points are constructed. The coordinate data of the detected plurality of candidate points and vector data that represent the directions of the blood vessel branches are stored in the memory, along with identifiers for the candidate points and the blood vessel branches. Next, the shapes of the coronary arteries are discriminated in detail based on the values of the surrounding voxels (CT values) for each detected candidate point. More specifically, the outlines (the outer walls of the blood vessels) of the coronary arteries are discriminated within cross sections perpendicular to the pathways of the coronary arteries. The discrimination of shapes is performed employing a known segmentation method, such as the Graph Cuts method. Data necessary to specify the extracted coronary artery regions are generated by the above processes. The generated data are stored in the memory.

Figure 6:
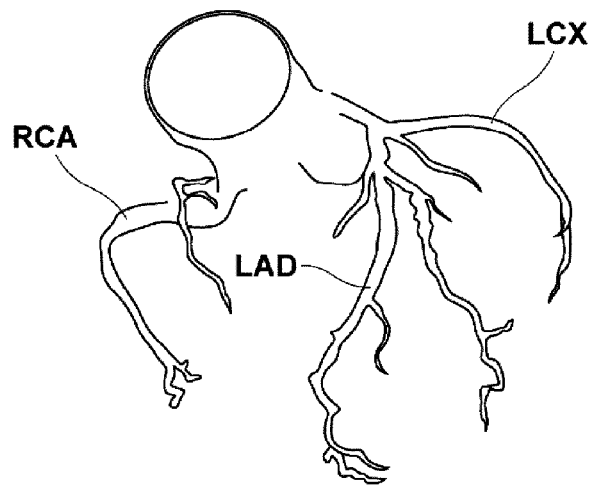
FIG. 6 is a diagram that illustrates an example of extraction results of a cardiac region extracting process and a coronary artery extracting process.

FIG. 6 is a diagram that illustrates an example of coronary arteries extracted by the above process. The coronary artery region is constituted by three main branches, a left anterior descending artery (hereinafter, referred to as "LAD"), a left circumflex coronary artery (hereinafter, referred to as "LCX region"), and a right coronary artery (hereinafter, referred to as "RCA region").

Note that in the present embodiment, the diagnosis assisting apparatus 1 displays the extracted coronary artery regions on the screen of a display device after executing the above procedures. On this screen, the user is enabled to correct the pathways of the displayed coronary artery regions, and manually set coronary artery pathways which were not extracted by the automated process. The diagnosis assisting apparatus 1 corrects the data regarding the coronary arteries stored in the memory based on user operations, if the user operations performed with respect to the screen are detected. In addition, the coronary artery regions which are displayed on the screen are updated based on the corrected data. The coronary artery extracting process 14 is completed when a user operation that confirms the regions is detected.

Next, the diagnosis assisting apparatus 1 executes a coronary artery governed region estimating process 15 with respect to the coronary artery regions extracted by the coronary artery region extracting process 14 and regions in the vicinities thereof.

The coronary artery governed region estimating process 15 estimates regions (coronary artery governed regions) which are exclusively governed by each of the LAD region, the LCX region, and the RCA region extracted by the coronary artery extracting process 14, based on each of the extracted regions. In the case that the user has corrected the extracted coronary artery regions, the coronary artery governed regions are estimated based on the corrected regions. At the same time, non governed regions, which are regions other than the coronary artery governed regions, are estimated. Boundary data that represents the boundaries among the coronary artery governed regions and the non governed regions are stored in the memory 3 as volume data, along with the extraction results of the coronary artery regions.

Figure 7:
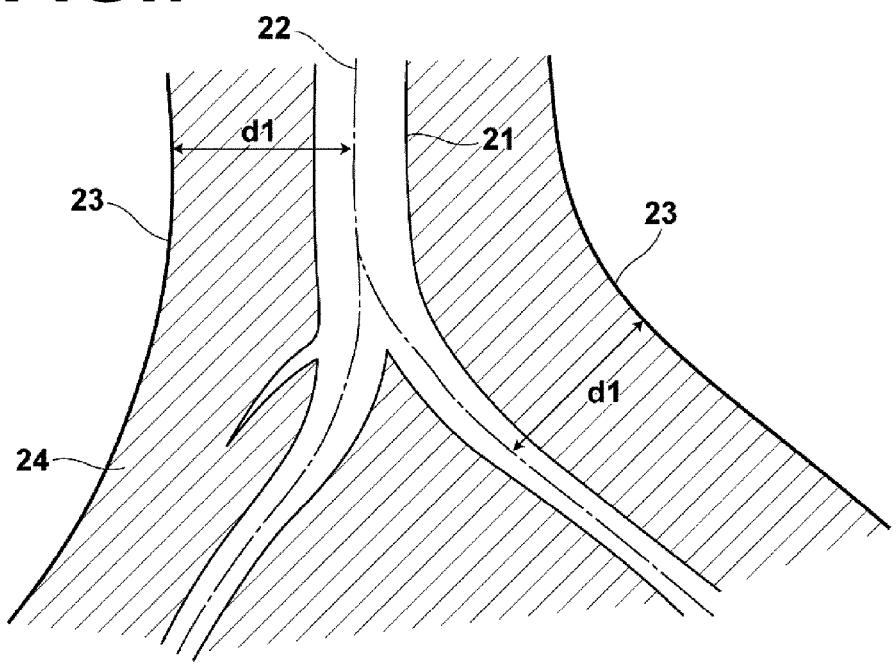
FIG. 7 is a diagram that illustrates an example of a method for estimating a coronary artery governed region.
Figure 8:
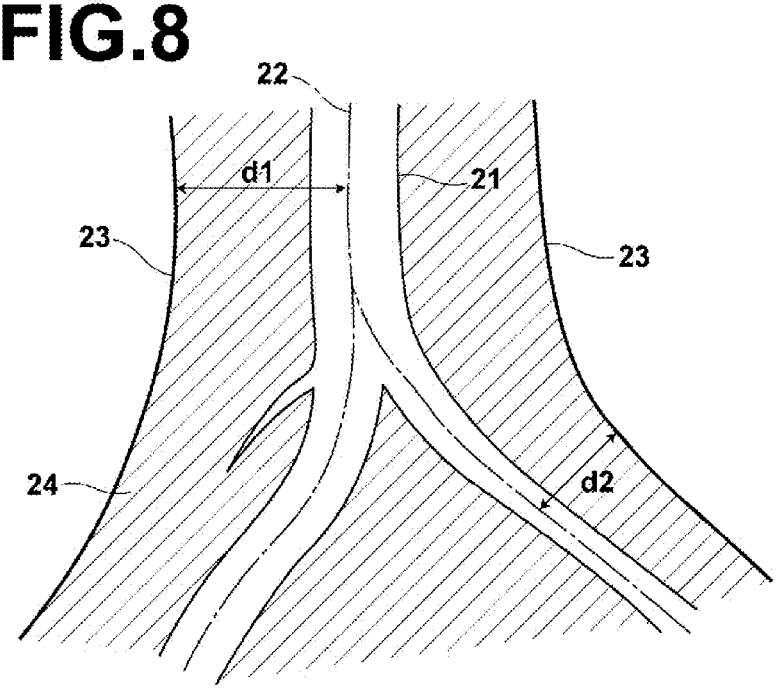
FIG. 8 is a diagram that illustrates another example of a method for estimating a coronary artery governed region.

FIG. 7 and FIG. 8 are diagrams that illustrate examples of relationships among coronary arteries 21 and coronary artery governed regions 24. In the example of FIG. 7, the width of the coronary artery governed region 24, that is, the distance between the boundaries 23 of the blood vessel governed regions 24 (the boundaries of the non governed regions) and the centerlines 22 of the coronary arteries 21 is uniformly set at width d1, regardless of the diameter of the coronary arteries 21. On the other hand, in the example of FIG. 8, the width of the coronary artery governed region 24 depends on the thickness of the coronary arteries 21. That is, the width d1 of the coronary artery governed region 24 where the coronary artery 21 is thick is greater than the width d2 of the coronary artery governed region 24 where the coronary arteries 21 are thin.

Because the range which is governed by coronary arteries is wider where the coronary arteries are thicker, it is preferable for the coronary artery governed region estimating process 15 to be performed such that the coronary artery governed region becomes a region such as that illustrated in FIG. 8, when accuracy of analysis is to be prioritized. However, if the coronary artery governed region extracting process 15 is performed such that the coronary artery governed region becomes a region such as that illustrated in FIG. 7, the processing time is shortened because the diameters of the coronary arteries need not be considered. Therefore, the estimating process may be performed under the assumption that the width of the coronary artery governed region is uniform, when high speed processing is prioritized.

In the present embodiment, the boundaries of the coronary artery governed region, that is, the widths d1 and d2, are estimated by the following processes. As described previously, the coronary artery extracting process 14 obtains positional data regarding the plurality of candidate points that represent the pathway of the coronary arteries 21, and the directions of the main axes of the coronary arteries. The diagnosis assisting apparatus 1 sets the centerlines 22 of the coronary arteries in the coronary artery governed region extracting process 15, based on the positional data regarding the plurality of candidate points.

Next, the diagnosis assisting apparatus 1 obtains coordinate points, which are separated for a distance $\Delta d$ from each of the plurality of candidate points that constitute the centerlines 22 in directions perpendicular to the main axis directions of the coronary arteries and along the surface of the myocardium. The plurality of coordinate points represent preliminary boundary lines of the coronary artery governed region. That is, coronary artery governed regions having widths of $\Delta d$ are set preliminarily.

Thereafter, the diagnosis assisting apparatus 1 judges whether any overlapping regions exist among the plurality of preliminarily set coronary artery governed region (the LAD region, the LCX region, and the RCA region), based on the positional relationships among the preliminary boundary lines which are set for each coronary artery. In the case that no overlapping regions exist among the plurality of coronary artery governed regions, the preliminary boundary lines are reset at distances $2\Delta d$ from the candidate points. Similar processes are repeated until overlapping regions appear among the plurality of coronary artery governed regions. If the width of the region when overlapping occurs is $n\Delta d$ (n is a positive integer), regions having widths $(n-1)\Delta d$, which were preliminarily set in the immediately preceding step, is estimated to be the coronary artery governed regions. Alternatively, regions having widths which were preliminarily set two or more steps previously may be estimated to be the coronary artery governed regions.

In the case that the coronary artery governed regions having a uniform width are estimated as in the example illustrated in FIG. 7, $\Delta d$ may be a constant value regardless of the thickness of the coronary arteries. On the other hand, in the case that it is desired to cause the widths of the coronary artery governed regions to depend on the thicknesses of the coronary arteries, the diameters of the coronary arteries are calculated at each candidate point that constitutes the centerlines of the coronary arteries. Alternatively, the diameters of the coronary arteries may be calculated in advance during the coronary artery extracting process 14. If the radius of the coronary artery at candidate point A is designated as ra, and the radius of the coronary artery at candidate point B is designated as rb (ra>rb), the widths of preliminary regions can be spread in increments of $\Delta da$ at candidate point A, and in increments of $\Delta db$ at candidate point B ($\Delta da > \Delta db$), to estimate coronary artery governed regions as illustrated in FIG. 8.

Note that in the present embodiment, short branches (such as the branch that protrudes toward the left in FIG. 7 and FIG. 8) are not considered, and the aforementioned processes are performed only with respect to main branches, as illustrated in the examples of FIG. 7 and FIG. 8. However, it is possible to set centerlines and to perform the aforementioned processes with every blood vessel branch. In addition, the aforementioned processes may be performed with the boundaries of the blood vessel regions (the blood vessel walls) as reference points instead of the centerlines.

Figure 9:
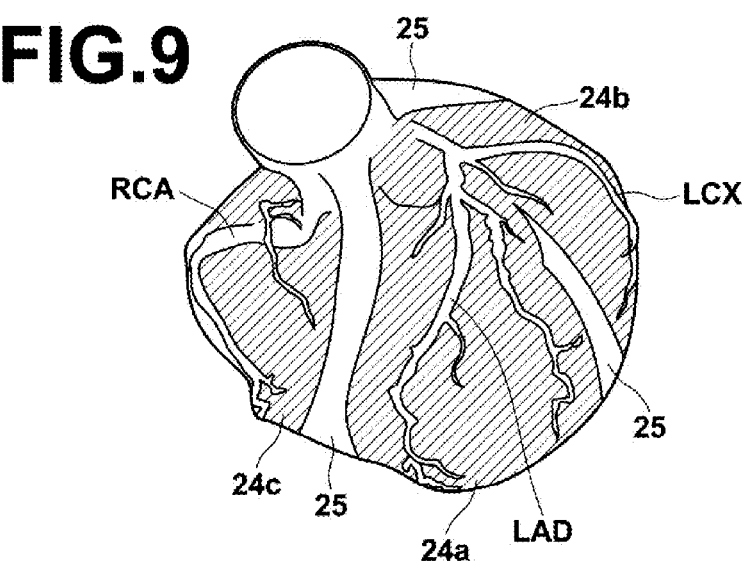
FIG. 9 is a diagram that illustrates an example of coronary artery governed regions and non governed regions.

FIG. 9 is a diagram that illustrates an example of the processing results of the coronary artery governed region extracting process 15 described above. By setting boundary lines by the aforementioned processes, an LAD governed region 24a, an LCX governed region 24b, and an RCA governed region 24c are estimated, and at the same time, non governed regions 25 are estimated, as illustrated in FIG. 9. The processing results obtained here are stored in the memory 3.

Note that in the present embodiment, the diagnosis assisting apparatus 1 displays the processing results illustrated in FIG. 9 on the screen of the display device after the aforementioned processes are executed. In this screen, the user is enabled to manually correct the outlines of the LAD governed region 24a, the LCX governed region 24b, and the RCA governed region 24c. The diagnosis assisting apparatus 1 corrects the processing results stored in the memory based on user operations, if such user operations with respect to the screen are detected. In addition, the LAD governed region 24a, the LCX governed region 24b, and he RCA governed region 24c which are displayed on the screen are updated based on the corrected data. The coronary artery governed region extracting process 15 is completed when a user operation that confirms the regions is detected.

In the present embodiment, the user may perform an operation to return to the screen that displays the extraction results for the coronary arteries, from the screen on which the processing results are displayed. That is, in the case that the user is not satisfied with the results of the coronary artery governed region extracting process 15, not only can the estimated governed regions be directly corrected, but the process can be redone from the coronary artery region extraction step. In the case that the user enters a command to perform the coronary artery region extracting process again, or corrects the extracted coronary artery regions, then confirms the regions, the diagnosis assisting apparatus 1 estimates the governed regions and the non governed regions based on the newly extracted or corrected LAD region, LCX region and RCA region, and updates the processing results which are stored in the memory.

Next, the diagnosis assisting apparatus 1 executes a coronary artery bulls eye image generating process 16, utilizing the extraction results of the coronary artery regions which are stored in the memory 3 as volume data. In the coronary artery bulls eye image generating process 16, the diagnosis assisting apparatus 1 defines the long axis A1, the short axis A2, the cross sections P1 through Pn, and the radial line segments l1 through lm in the same manner as in the cardiac function analyzing process 12 which was described with reference to FIG. 3 and FIG. 4. Alternatively, the diagnosis assisting apparatus 1 refers to data regarding the long axis, the short axis, the cross sections, and the line segments which were defined in the cardiac function analyzing process 12 and stored in the memory 3, to obtain this data.

Figure 10:
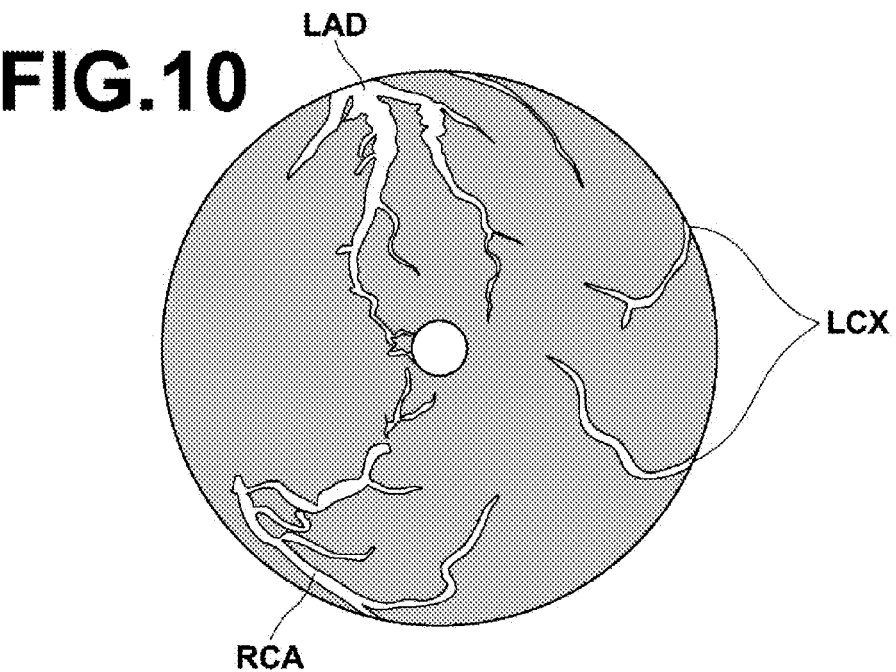
FIG. 10 is a diagram that illustrates an example of a coronary artery bulls eye image.

Thereafter, the diagnosis assisting apparatus 1 searches for the maximum values from among the voxel data along the radial line segments l1 through lm within each cross section Pi and within a predetermined distance from intersecting points C. That is, MIP (Maximum Intensity Projection) processes are executed along each of the line segments l1 through lm. Thereby, coronary image data of coronary arteries that extend within the cross sections or that intersect the cross sections are obtained. The diagnosis assisting apparatus 1 arranges the coronary artery image data along the circumferences of concentric circles having a different radius for each cross section, to generate a coronary artery bulls eye image. In the present embodiment, the apex of the heart is set as the center of the concentric circles, the coronary artery image data of the cross section Pn, which is closest to the apex of the heart, are arranged along the circumference of a circle having the smallest radius, and the coronary artery image data of the cross section P1, which is furthest from the apex of the heart, are arranged along the circumference of a circle having the largest radius. FIG. 10 is a diagram that illustrates an example of a coronary artery bulls eye image.

Figure 11:
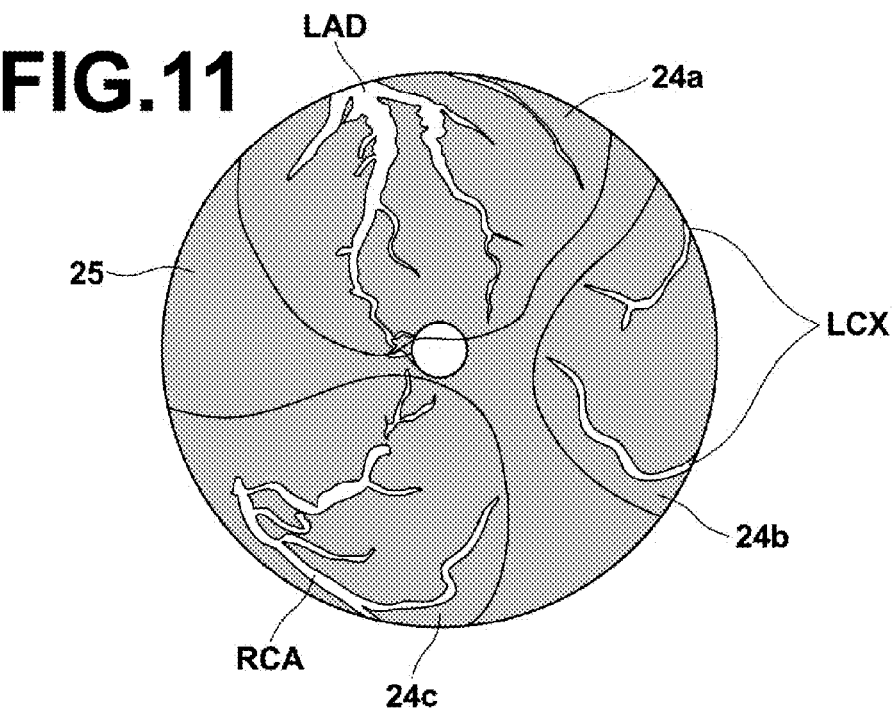
FIG. 11 is a diagram that illustrates an example of a coronary artery bulls eye image that includes boundaries among coronary artery governed regions and non governed regions.

In addition, the diagnosis assisting apparatus 1 also performs a process of arranging the boundary data, which were stored along with the extraction results of the coronary artery regions in the coronary artery governed region extracting process 15, onto the circumferences of the concentric circles having different radii for each cross section. FIG. 11 is a diagram that illustrates an example of a bulls eye image that includes boundaries among the LAD governed region 24a, the LCX governed region 24b, the RCA governed region 24c, and the non governed regions 25. In the present embodiment, the bulls eye image including the boundaries illustrated in FIG. 11 is stored separately from the bulls eye image illustrated in FIG. 10, and is selectively utilized in a display process to be described later.

The diagnosis assisting apparatus 1 performs an index value calculating process 17, employing the three dimensional function image 8 and the boundary data which were estimated and stored in the coronary artery governed region extracting process 15. That is, index values which are useful to aid diagnosis are derived, by analyzing the evaluation values that constitute the three dimensional functional image 8, utilizing the boundary data. Note that new index values may be derived by analyzing the evaluation values that constitute the cardiac function bulls eye image while utilizing the boundary data, instead of the evaluation values that constitute the three dimensional functional image.

Calculation of the index values is performed only employing evaluation values which are included in the LAD governed region 24a, the LCX governed region 24b, and the RCA governed region 24c, which are estimated in the coronary artery governed region extracting process 15. That is, evaluation values which are included in the non governed regions 25 are not referred to in the index value calculating process 17, and such evaluation values are not employed to calculate the index values.

The index values are values that represent the influence that blood flow from the coronary arteries impart onto cardiac functions.

The following index values may be calculated and displayed, for example.

In the case that the evaluation values that constitute the three dimensional functional image 8 and the cardiac function bulls eye image are evaluation values that indicate whether cardiac activity is normal, such as:

Amount of wall movement: a value that represents displacement in the positions of the myocardial walls during expansion and contraction of the heart;

Amount of wall thickness variation: the difference in myocardial wall thickness between heart expansion and heart contraction;

Percentage of wall thickness increase: a value that represents the ratio between the wall thickness variation and the wall thickness during heart expansion; and Amount of wall activity: a value that represents the difference in ventricle diameter between heart expansion and heart contraction, the index values may be respective average values of the evaluation values which are included in each of the LAD governed region, the LCX governed region, and the RCA governed region. The average may be a simple mean value, or a weighted average, in which the evaluation values are weighted according to the distances from the coronary arteries.

For example, if the average value of the amount of wall activity is markedly smaller in the LCX governed region than in the other two governed regions, cardiac functions are only deteriorated within the LCX governed region. In this case, a hypothesis that an abnormality such as occlusion is present in the LCX, which governs the cardiac functions in the LCX governed region, can be established. That is, the abnormal portions of the heart can be segmented by comparisons of three numerical values, and the coronary artery which is suspected of being abnormal can be estimated.

In the case that the evaluation values that constitute the three dimensional functional image 8 and the cardiac function bulls eye image is:

Ejection ratio: a ratio between the amount of blood which is pumped during a single contraction and the volume of the heart during expansion the minimum value included in each of a region, in which the LAD governed region and the LCX governed region are combined (hereinafter, referred to as "LCA governed region"), and the RCA governed region are obtained.

For example, in the case that the minimum value of the ejection ratio within the LCA governed region is markedly smaller than the minimum value of the ejection ratio in the RCA governed region, an abnormality may be suspected in either the cardiac muscles that surround the left ventricle or in the valve of the left ventricle. In the case that no particular abnormality is found in the LAD and the LCX, then a hypothesis that there is a high probability that the valve is abnormal can be established. That is, the abnormal portions of the heart can be segmented by comparing the two numerical values, and further, the type of illness can also be estimated.

In addition to the average and minimum values of the evaluation values, maximum values and sums of the evaluation values may be calculated as the index values, depending on the types of the evaluation values. Note that a single index value may be obtained for each coronary artery governed region, as in the aforementioned example in which the average value was employed as the index value. Alternatively, a single index value may be obtained for a plurality of coronary artery governed regions, as in the aforementioned example in which the minimum value was employed as the index value.

Next, a display control process 18 which is performed by the diagnosis assisting apparatus 1 will be described. In the present embodiment, the diagnosis assisting apparatus 1 selects one of the following display modes described below, by referring to setting data regarding a display mode stored in the memory 3, or by detecting menu selection operations by a user, then controls the display format and the display timing (switching of display) of the screen.

In the case that display of bulls eye images is requested, the diagnosis assisting apparatus 1 displays the coronary artery bulls eye image overlapped on the cardiac function bulls eye image. In this case, the degree of transparency of each of the bulls eye images are set such that data included in both the coronary artery bulls eye image and the cardiac function bulls eye image can be observed. As described previously, a coronary artery bulls eye image that includes the boundary data of the coronary artery governed regions and a coronary artery bulls eye image that does not include the boundary data are stored in the memory 3. The diagnosis assisting apparatus 1 determines which coronary artery bulls eye image is to be displayed overlapped on the cardiac function bulls eye image according to setting data or user input.

In the case that display of volume rendered images is requested, the diagnosis assisting apparatus 1 displays the extraction results of the cardiac region and the coronary artery regions overlapped on the three dimensional functional image. Further, the boundary data is displayed overlapped onto the three dimensional functional image according to setting data or user input.

In addition, the diagnosis assisting apparatus 1 displays the index values which have been calculated in the index value calculating process 17. In the case that a plurality of types of index values have been calculated for each of the plurality of regions, all of the calculated index values may be displayed simultaneously, according to settings. Alternatively, only a single type of index value may be displayed, and switching to display other types of index values may be effected by user input. In addition, in cases that simultaneous display of the images and the index values are requested, the diagnosis assisting apparatus 1 determines whether to display the index values arranged alongside the images or overlapped therewith, according to setting data or user input.

Figure 12:
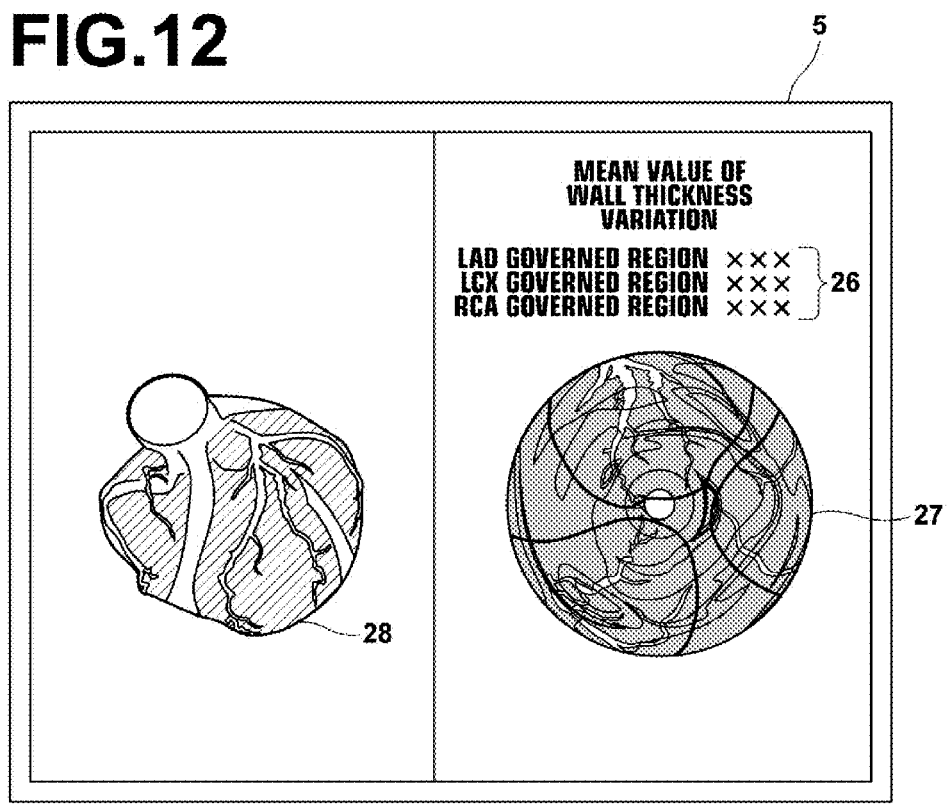
FIG. 12 is a diagram that illustrates an example of a manner in which index values are displayed.

The example of a manner of display illustrated in FIG. 12 is that in which the calculated index values 26 and an overlapped image 27 in which the coronary artery bulls eye image and the cardiac function bulls eye image are overlapped are displayed on the right half of the screen, and an image 28 that shows the relationships among the coronary artery governed regions and the non governed regions are displayed on the left half of the screen. Note that FIG. 12 illustrates an example in which the coronary artery bulls eye image is larger than the cardiac function bulls eye image. However, the sizes of the two bulls eye images may be the same, or the cardiac function bulls eye image may be larger than the coronary artery bulls eye image.

As described above, the manner of display may be changed by settings or by user input. Other possible manners of display include that in which the index values 26 are overlapped on the regions that they correspond to on the overlapped image 27, that in which the index values are displayed only when a cursor is placed within the coronary artery governed regions within the overlapped image 27, and that in which the overlapped image 27 and the index values 26 are displayed at the center of the screen.

In addition, an alternate manner of display may be considered, in which display of the overlapped image 27 and the image 28 that shows the relationships among the coronary artery governed regions and the non governed regions are omitted, and only the index values are displayed. When a group of subjects including healthy patients are to be diagnosed following a group examination, for example, first, a simple diagnosis may be performed by displaying a list of the index values for the plurality of subjects. Then, overlapped images may be displayed on the screen only for subjects for whom it is judged that more detailed observation is necessary. In this case, efficient diagnosis can be performed for a great number of subjects.

As described above, the diagnosis assisting apparatus and the diagnosis assisting program of the present embodiment displays evaluation values in an easily observable format, and index values for each region, which are derived by analyzing the evaluation values, are displayed. For this reason, regions in which deterioration of functions is conspicuous can be specified easily. Further, the coronary artery which is suspected of being abnormal and the type of disease can also be easily estimated.

In conventional methods, all of the evaluation values that constitute three dimensional functional images or functional bulls eye images were employed to perform analysis. For this reason, only index values that included noise were obtainable as the results of analysis. In contrast, the present embodiment employs only evaluation values within regions in which the relationships between the coronary arteries and cardiac functions are clear (regions governed by each coronary artery) to perform analysis. Thereby, index values, which are positively useful in judging the relationships among abnormalities in coronary arteries and deterioration in cardiac functions, can be obtained.

In addition, the diagnosis assisting apparatus and the diagnosis assisting program of the present embodiment estimates coronary artery governed regions and non governed regions based on coronary artery regions, which are extracted not from functional images but from anatomical images. Therefore, the regions can be set accurately. Further, the accurately set regions are employed as units of analysis, thereby enabling obtainment of highly reliable index values.

Embodiment 2

As described above, the evaluation values represented by the three dimensional functional image 8 include evaluation values which are calculated from a single three dimensional anatomical image, such as wall thickness. Meanwhile, there are evaluation values, such as amount of wall movement, amount of wall thickness variation, and ejection rate, which are calculated by analyzing a plurality of three dimensional anatomical images in temporal sequence. The diagnosis assisting apparatus 1 of the first embodiment extracts the LAD region, the LCX region, and the RCA region, which are the bases for estimation of the coronary artery governed regions, from a single three dimensional anatomical image. In the case that the evaluation values of the three dimensional functional image are evaluation values such as wall thickness, which are calculated form a single three dimensional anatomical image, each of the governed regions can be accurately estimated, by executing the coronary artery extracting process 14 and the coronary artery governed region estimating process 15 using the same three dimensional anatomical image which was employed to generate the functional image.

However, in the case that the evaluation values are values which are calculated based on a plurality of three dimensional anatomical images of different phases, such as the amount of wall movement, determining which three dimensional anatomical image to use for the coronary artery extracting process 14 and the coronary artery governed region estimating process 15 becomes a problem. The pathways of the coronary arteries change according to the movement of the heart, and therefore, the extraction results for the LAD region, the LCX region, and the RCA region of the coronary artery extracting process 14 will vary according to the selected phase.

The diagnosis assisting apparatus of the second embodiment differs form the diagnosis assisting apparatus of the first embodiment in that it performs processes suited for cases in which the three dimensional functional image is an image that represents evaluation values calculated by analyzing a plurality of three dimensional anatomical images of different phases. Hereinafter, a description of the diagnostic assisting apparatus of the second embodiment will be given focusing on the differences from that of the first embodiment, and descriptions of elements which are the same as those of the first embodiment will be omitted.

Figure 13:
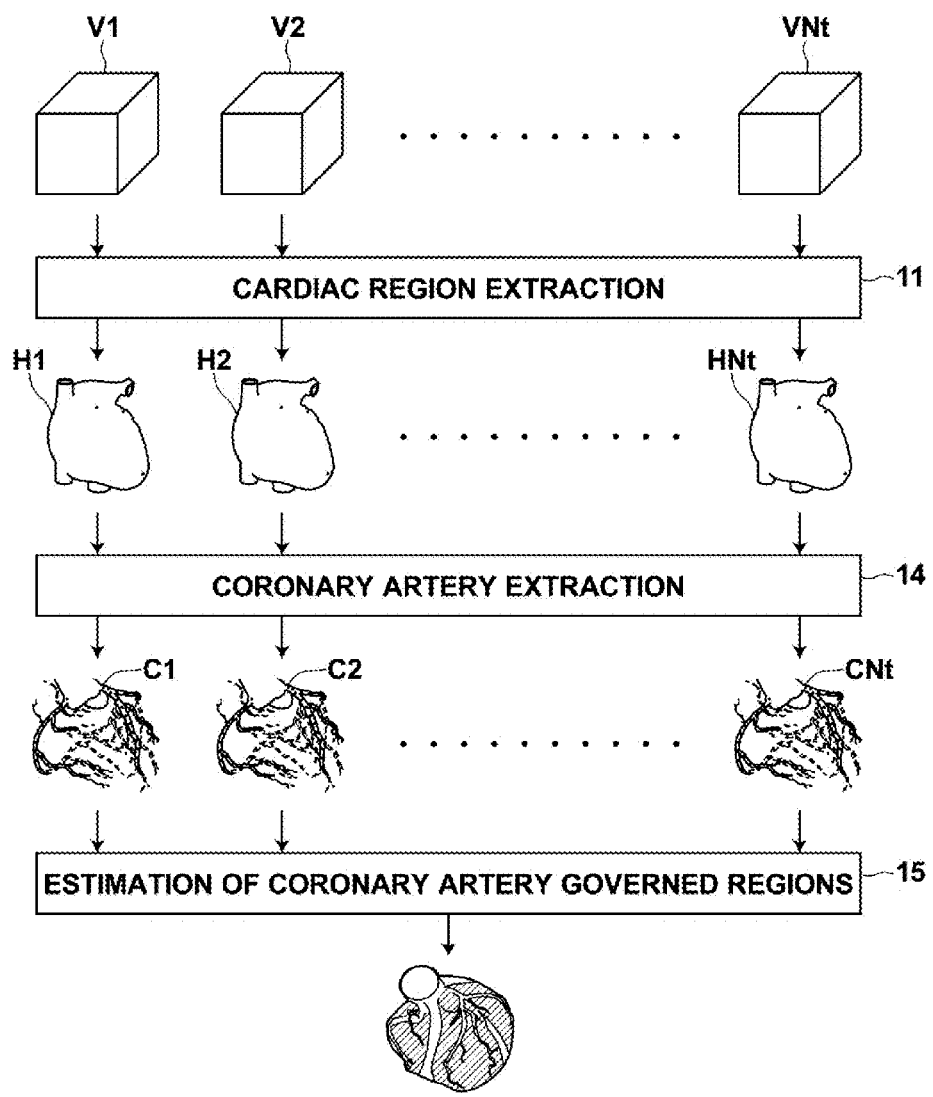
FIG. 13 is a diagram that illustrates the procedures for estimating coronary artery governed regions employing a plurality of three dimensional anatomical images.

FIG. 13 is a diagram that illustrates a process performed by the diagnosis assisting apparatus that differs form those illustrated in FIG. 2. The procedure illustrated in FIG. 13 is that in which coronary artery governed regions are estimated employing a plurality (Nt) three dimensional anatomical images. Images corresponding to 10 to 20 phases are generally obtained during EKG synchronized imaging of the heart. Therefore, the number Nt of three dimensional anatomical images is generally 10 to 20.

As illustrated in FIG. 13, the diagnosis assisting apparatus of the second embodiment executes the cardiac region extracting process 11 with respect to each of the Nt three dimensional anatomical images V1 through VNt, to extract Nt cardiac regions H1 through HN1 of different phases. Next, the coronary artery extracting process 14 is executed on each of the Nt cardiac regions H1 through HN1 of different phases, to extract Nt coronary artery regions C1 through CNt of different phases. Then, a single LAD governed region, a single LCX governed region, a single RCA governed region, and non governed regions other than these regions are estimated based on the Nt coronary artery regions C1 through CNt of different phases in the coronary artery governed region estimating process 15. That is, in the second embodiment, processing results are output for each phase by the cardiac region extracting process 11 and the coronary artery extracting process 14, while a single processing result that does not depend on the phase is output by the coronary artery governed region estimating process 15.

Hereinafter, the coronary artery governed region estimating process 15 as executed by the second embodiment will be described in detail with reference to FIGS. 14 through 16. Note that in the following description, a case will be described in which Nt=3, for the sake of convenience. I, II, and III of FIG. 14 are diagrams that illustrate examples of coronary artery governed regions for different phases. In these diagrams, the coronary artery regions C1 through C3 are regions which have been extracted from three dimensional anatomical images V1 through V3 of different phases, respectively. However, the diagrams only illustrate a portion of the coronary artery regions C1 through C3 of different phases. Coronary artery governed regions R1 through R3 are governed regions which are estimated based on the coronary artery regions C1 through C3 of different phases, respectively. However, the diagrams only illustrate a portion of the coronary artery governed regions R1 through R3 of different phases.

The coronary artery regions C1 through C3 of different phases are regions that represent the same anatomical blood vessel. However, as described previously, the pathways of coronary arteries change accompanying movement of the heart. Therefore, the shapes of the coronary artery regions C1 through C3 of different phases differ according to the phase. In addition, the coronary artery governed regions are estimated based on the coronary artery reasons. Therefore, the shapes of the coronary artery governed regions R1 through R3 of different phases also differ according to the phase.

In the second embodiment, a product (an AND region) or a sum (an OR region) of the coronary artery governed regions R1 through R3 is obtained, and the obtained region is estimated to be a coronary artery governed region. FIG. 15A is a diagram that illustrates an example of a product of coronary artery governed regions of different phases. The product region is a region which is estimated to be a governed region in all of the phases. Accordingly, the index values which are calculated using only the evaluation values within the product region strongly reflect the influence imparted on cardiac function by the coronary arteries.

FIG. 15B is a diagram that illustrates an example of a sum of coronary artery governed regions of different phases. The sum region is a region which is estimated to be a governed region in at least one of the phases. Accordingly, there is a higher possibility that the sum region includes more noise compared to the product region. However, the sum region is suited for cases in which it is desired to calculate index values using evaluation values related to a wider range. More specifically, the sum region includes a region which is estimated to be a governed region in all phases, a region which is estimated to be a governed region in not all but a plurality of phases, and a region which is estimated to be a governed region in a single phase. Accordingly, when calculating index values using the evaluation values within the sum region, index values having degrees of accuracy equivalent to those of index values calculated from evaluation values within a product region can be calculated, by weighting the evaluation values according to the number of overlapping coronary artery governed regions the evaluation values are located in.

Figure 16:
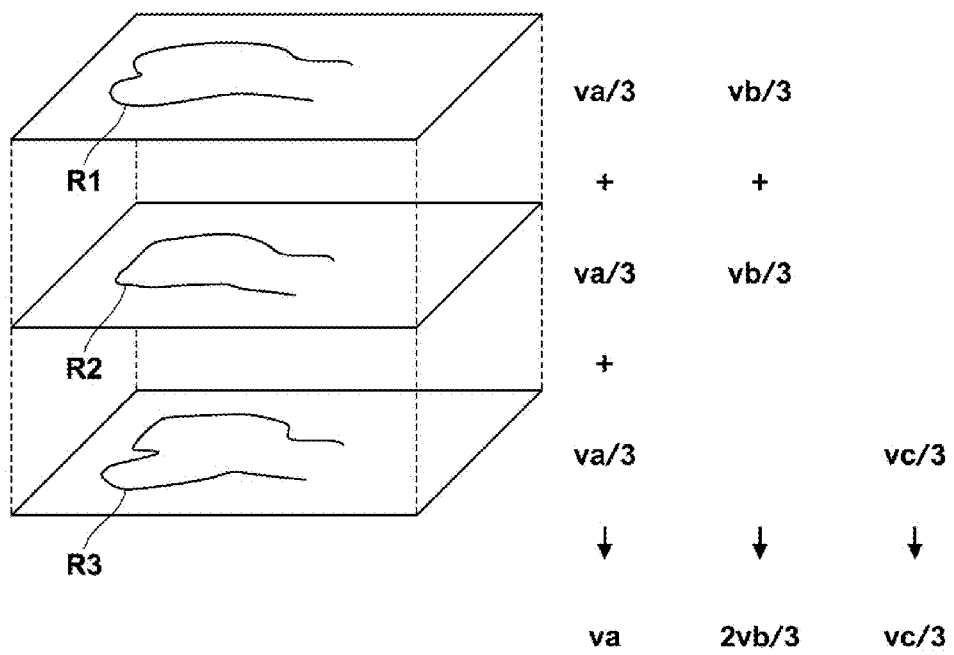
FIG. 16 is a diagram for explaining weighting of evaluation values.

FIG. 16 is a diagram for explaining the weighting of evaluation values, and illustrates three coronary artery governed regions R1 through R3 of different phases that constitute a sum region. Note that in FIG. 16, the coronary artery governed regions R1 through R3 are illustrated as planar regions for the sake of convenience. However, the actual coronary artery governed regions R1 through R3 are regions which are curved along the outer wall of the heart.

As illustrated in FIG. 16, in the second embodiment, values, which are the values of voxel data that constitute the coronary artery governed regions of different phases divided by Nt, are employed as the evaluation values of the coronary artery governed regions of different phases. For example, when Nt=3, the evaluation values of voxel data having values of va, vb, and vc are va/3, vb/3, and vc/3, respectively. The evaluation values within the sum regions are the totals of the evaluation values of the evaluation values within the coronary artery governed regions of different phases. In a range within the sum region where the three coronary artery governed regions of different phases overlap, three values which have been divided by three are added, and therefore, the evaluation value assumes the same value as that of the original voxel data (va in the example illustrated in FIG. 16). In a range within the sum region where two coronary artery governed regions of different overlap, two values which have been divided by three are added, and therefore, the evaluation value assumes a value ⅔ that of the original voxel data. In a range where no overlapping occurs among the coronary artery governed regions of different phases, the evaluation value assumes a value ⅓ that of the original voxel data.

As a result, the values of each piece of voxel data that constitute the sum region are weighted such that voxel data included in ranges having greater numbers of overlaps are more heavily weighted. Thereby, the influence that noise, which is included in ranges having small numbers of overlaps, imparts on the calculation results of the index values is reduced. The index value calculating process calculates average values, obtains minimum values, or obtains maximum values within the sum region after executing the weighting process (the adding process), to obtain highly reliable index values. Note that the index value calculating process may alternatively calculate average values, obtain minimum values, or obtain maximum values of the values of voxel data within the sum region, without performing weighting according to the number of overlaps.

According to the process described above, regions governed by blood vessels can be accurately estimated even in organs, such as the heart, in which the pathways of the coronary arteries change during each phase of movement. Particularly, the product region of the coronary artery governed regions of different phases is that which is estimated to be a governed region in every phase. Therefore, the degree of certainty that the product region is a region of which the functions are governed by the blood vessel is high, and the reliability of index values calculated based on the product region is extremely high. In addition, highly reliable index values may also be obtained based on the sum region of the coronary artery governed regions of different phases, if the index values are calculated after the evaluation values included therein are weighted according to the number of overlaps.

Other Embodiments

In the embodiments described above, the coronary artery regions were extracted from the three dimensional anatomical image 7, and the coronary artery governed regions were estimated within the three dimensional anatomical image 7, based on the extracted coronary artery regions. In addition, the index values were calculated employing the evaluation values that constitute the three dimensional functional image 8. An alternate embodiment, in which the coronary artery governed regions are estimated from within the coronary artery bulls eye image after the coronary artery bulls eye image is generated, and the index values are calculated employing the evaluation values that constitute the coronary artery bulls eye image, may be considered.

In addition, in the embodiment described above, the apex of the heart is set as the center of the concentric circles, values obtained with regard to the cross section Pn, which is closest to the apex of the heart, are arranged along the circumference of a circle having the smallest radius, and values obtained with regard to the cross section P1, which is furthest from the apex of the heart, are arranged along the circumference of a circle having the largest radius. Alternatively, the base of the heart may be set as the center of the concentric circles, values obtained with regard to the cross section P1 may be arranged along the circumference of a circle having the smallest radius, and values obtained with regard to the cross section Pn may be arranged along the circumference of a circle having the largest radius. With regard to bulls eye images, various other modifications are known. Any such known modification may be applied to the present invention.

In the embodiment described above, the series of processes were built into and executed by a single computer. However, the series of processes may be divided among a plurality of computers, to construct a diagnosis assisting system having functions equivalent to those of the diagnosis assisting apparatus 1.

The embodiments described above may further be equipped with print outputting means or data outputting means (recording onto media such as CD-R's and DVD's, or data transfer via networks), in addition to the display control means. That is, in the present invention, the manner of output of the index values is not limited to display on the screen.

The embodiments described above were described as examples in which the organ was a heart and the main branches were coronary arteries. However, the present invention is not limited to assisting diagnosis of cardiac functions, and may be applied to assist diagnosis of other organs, such as the brain and the liver. It would be clear to those skilled in the art that the method for extracting the coronary artery regions and the method for estimating the coronary artery governed regions may be applied to extract other blood vessel regions and to estimate blood vessel governed regions.

In this manner, the present invention is not limited to the embodiment described above. Various changes and modifications are possible, as long as they do not stray from the spirit and scope of the present invention.

What is claimed is:
1. A diagnosis assisting apparatus, comprising:
image storage means, for storing three dimensional functional images, in which evaluation values regarding functions of organs are arranged three dimensionally along the shape of the organs, and for storing three dimensional anatomical images that represent the structures of the organs three dimensionally;
blood vessel region extracting means, for extracting at least one blood vessel region that represents at least one blood vessel that governs the functions of the organs;
blood vessel governed region estimating means, for estimating blood vessel governed regions within which organ functions are governed by the blood vessels and for estimating regions other than the blood vessel governed regions as non governed regions, based on each of the blood vessel regions;
index value calculating means, for calculating index values to be indices of diagnosis by analyzing the evaluation values that constitute the three dimensional functional image, that calculates the index values without using the evaluation values included in the non governed regions; and output control means, for outputting the index values calculated by the index value calculating means.

2. A diagnosis assisting apparatus as defined in claim 1, wherein:

the blood vessel region extracting means extracts blood vessel regions that represent branched blood vessels and are constituted by Nb (Nb is an integer having a value of at least 1) main branched regions from the three dimensional anatomical images; and the blood vessel governed region estimating means estimates blood vessel governed regions within which organ functions are governed by the main branched regions and estimates regions other than the blood vessel governed regions as non governed regions, based on each of the main branched regions.

3. A diagnosis assisting apparatus as defined in claim 2, wherein:

the image storage means stores Nt (Nt is an integer having a value of at least 2) three dimensional anatomical images, each of which represents the structures of each organ in a different phase;

the blood vessel region extracting means extracts the blood vessel regions from each of the Nt three dimensional anatomical images;

the blood vessel governed region estimating means estimates blood vessel governed regions within which organ functions are governed by Nb main branched regions that constitute each of the Nt extracted blood vessel regions, based on each of the Nb main branched regions, obtains one of a product and a sum of the Nt blood vessel governed regions within different phases, which are estimated for each of the Nb main branched regions within the Nt blood vessel regions, and estimates one of the product and the sum to be the blood vessel governed regions governed by blood vessels represented by the main branched regions.

4. A diagnosis assisting apparatus as defined in claim 3, wherein:

the index value calculating means weights evaluation values that constitute the three dimensional functional images according to the number of overlapping blood vessel governed regions within different phases, in the case that the blood vessel governed regions are sums of the Nt blood vessel governed regions within different phases.

5. A diagnosis assisting apparatus as defined in claim 1, wherein:

the blood vessel governed region estimating means estimates each blood vessel governed region such that one blood vessel governed region does not overlap another blood vessel governed region, in the case that the blood vessel regions are constituted by two or more main branched regions.

6. A diagnosis assisting apparatus as defined in claim 1, wherein:

the blood vessel governed region estimating means estimates the blood vessel governed regions to have wider widths as the thickness of the blood vessels becomes greater.

7. A diagnosis assisting apparatus as defined in claim 1, wherein:

the index value calculating means calculates index values for each of two or more blood vessel governed regions, in the case that the blood vessel regions are constituted by two or more main branched regions.

8. A diagnosis assisting apparatus as defined in claim 1, wherein:

the index value calculating means calculates at least one of the average value, the minimum value, and the maximum value of evaluation values included in the blood vessel governed regions as the index values.

9. A diagnosis assisting apparatus as defined in claim 1, further comprising:

bulls eye image generating means, for generating bulls eye images with respect to each of the three dimensional functional images and the three dimensional anatomical images; wherein:

the output control means causes a bulls eye image of the three dimensional functional image and the bulls eye image of the three dimensional anatomical image to be displayed overlapped on each other on the screen of a display device, and also causes the index values calculated by the index value calculating means to be displayed on the screen.

10. A diagnosis assisting apparatus as defined in claim 1, wherein:

the blood vessel governed region estimating means further displays the estimated blood vessel governed regions on the screen of a display device, detects user operations performed with respect to the screen, and updates the blood vessel governed regions based on the detected operations.

11. A diagnosis assisting apparatus as defined in claim 1, wherein:

the blood vessel region extracting means further displays the extracted blood vessel regions on the screen of a display device, detects user operations performed with respect to the screen, and corrects the extracted blood vessel regions based on the detected operations; and the blood vessel governed region estimating means estimates the blood vessel governed regions and the non governed regions based on corrected blood vessel regions, in the case that correction of the blood vessel regions is performed.

12. A diagnosis assisting apparatus as defined in claim 1, wherein:

the organs are hearts; and the blood vessels are coronary arteries.

13. A computer readable non-transitory storage medium storing a diagnosis assisting computer program, the computer program, when executed on at least one computer, causing the computer to perform a diagnosis assisting method, comprising the steps of:

reading out three dimensional functional images, in which evaluation values regarding functions of organs are arranged three dimensionally along the shape of the organs, and three dimensional anatomical images that represent the structures of the organs three dimensionally from a storage medium in which the three dimensional functional images and the three dimensional anatomical images are stored;

extracting at least one blood vessel region that represents at least one blood vessel that governs the functions of the organs;

estimating blood vessel governed regions within which organ functions are governed by the blood vessels and for estimating regions other than the blood vessel governed regions as non governed regions, based on each of the blood vessel regions;

calculating index values to be indices of diagnosis by analyzing the evaluation values that constitute the three dimensional functional image without using the evaluation values included in the non governed regions; and outputting the index values calculated by the index value calculating means.

14. A diagnosis assisting method executed by at least one computer, comprising the steps of:

reading out three dimensional functional images, in which evaluation values regarding functions of organs are arranged three dimensionally along the shape of the organs, and three dimensional anatomical images that represent the structures of the organs three dimensionally from a storage medium in which the three dimensional functional images and the three dimensional anatomical images are stored;

extracting at least one blood vessel region that represents at least one blood vessel that governs the functions of the organs;

estimating blood vessel governed regions within which organ functions are governed by the blood vessels and for estimating regions other than the blood vessel governed regions as non governed regions, based on each of the blood vessel regions;

calculating index values to be indices of diagnosis by analyzing the evaluation values that constitute the three dimensional functional image without using the evaluation values included in the non governed regions; and outputting the index values calculated by the index value calculating means.

* * * * *